US005494791A

United States Patent [19]

Cohen

[11] Patent Number: 5,494,791
[45] Date of Patent: Feb. 27, 1996

[54] MONOCLONAL ANTIBODIES AGAINST GLYCATED LOW DENSITY LIPOPROTEIN

[75] Inventor: Margo P. Cohen, New York, N.Y.

[73] Assignee: Exocell, Inc., Philadelphia, Pa.

[21] Appl. No.: 202,652

[22] Filed: Feb. 28, 1994

Related U.S. Application Data

[63] Continuation-in-part of Ser. No. 903,955, Jun. 26, 1992, abandoned.

[51] Int. Cl.$^6$ .................... G01N 33/535; G01N 33/577; G01N 33/92; C07K 16/44
[52] U.S. Cl. .................... 435/7.9; 435/7.94; 435/188; 435/240.27; 436/518; 436/536; 436/548; 436/71; 530/388.25; 530/391.1; 530/391.3
[58] Field of Search .................... 435/7.9, 7.94, 435/188, 240.27; 436/518, 536, 548.71, 815; 530/388.25, 391.1, 391.3

[56] References Cited

U.S. PATENT DOCUMENTS

| | | | |
|---|---|---|---|
| 4,629,692 | 12/1986 | Dean | 435/7.7 |
| 4,727,036 | 2/1988 | Knowles et al. | 530/387.9 |
| 4,797,473 | 1/1989 | Tarsio et al. | 530/388.25 |
| 4,876,188 | 10/1989 | Smith et al. | 435/7.25 |

FOREIGN PATENT DOCUMENTS

| | | |
|---|---|---|
| 0201187A1 | 3/1986 | European Pat. Off. . |
| 0230934A2 | 1/1987 | European Pat. Off. . |
| 0257421A2 | 8/1987 | European Pat. Off. . |
| 0315864A1 | 10/1988 | European Pat. Off. . |

OTHER PUBLICATIONS

Mullarkey, et al., "Free Radical Generation by Early Glycation Products: A Mechanism for Accelerated Atherogenesis in Diabetes", *Biochem. Biophys. Res. Comm.*, 173(3):932–939 (1990).

Gillery, et al., "Glycation of Proteins as a Source of Superoxide", *Diabete & Metabolisme (Paris)*, 14:25–30 (1988).

Quinn, et al., "Oxidatively Modified Low Density Lipoproteins. A Potential Role in Recruitment and Retention of Monocyte/Macrophages During Atherogenesis", *Proc. Natl. Acad. Sci. USA*, 84:2995–2998 (1987).

Sparrow, et al., "A Macrophage Receptor That Recognizes Oxidized Low Density Lipoprotein but Not Acetylated Low Density Lipoprotein", *J. Biol. Chem.*, 264(5):2599–2604 (1989).

Steinberg, et al., "Beyond Cholesterol: Modifications of Low–Density Lipoprotein That Increase Its Atherogenicity", *New England Journal of Medicine*, 3201(14):915–924 (1989).

Lecomte, et al., "Malondialdehyde Adducts to, and Fragmentation of, Apolipoprotein B From Human Plasma", *Clinica Chimics Acta* 218:39–46 (1993).

Clark, B. R. et al, "Enzyme–Linked Immunosorbent Assay (ELISA): Theoretical and Practical Aspects" in *Immunoenzyme techniques*, E. T. Maggio, ed. CRC Press, Inc. 1980, pp. 167–179.

Kortlandt, W. et al., "A simple method for the measurement of total and glycated apolipoprotein B and its relevance to apolipoprotein–B metabolism in diabetes mellitus", *Clinica Chimica Acta*, vol. 186, pp. 109–118, 1989.

Johnson, et al., "Fructosamine: A New Approach to the Estimation of Serum Glycosylprotein. An Index of Diabetic Control", *Clinica Chimica Acta*, 127:87–95 (1982).

San Gil, et al., "Improved Estimation of Fructosamine, as a Measure of Glycated Serum Protein, with the Technicon RA–1000 Analyzer", *Clin. Chem.*, 31(12):2005–2006 (1985).

Curtis, et al., "A Novel Method for Generating Region–specific Monoclonal Antibodies to Modified Proteins", *J. Clin Invest.*, 72:1427–1438 (1983).

Garlick, et al., "Characterization of Glycosylated Hemoglobins", *J. Clin. Invest.*, May 1982, pp. 1062–1072.

Nakayama, et al., "Quantitative Enzyme–Linked Immunosorbent Assay (ELISA) for Non–Enzymatically Glycated Serum Protein", *J. Immunol. Methods*, 99:95–100 (1987).

Shapiro, et al., "Sites of Nonenzymatic Glycosylation of Human Hemoglobin A", *J. Biol. Chem.*, 255:3120–3127 (1980).

Cohen et al., "Production and Characterization of Monoclonal Antibodies Against Human Glycoalbumin", *J. Immunol. Methods*, 117:121–129 (1989).

Elizabeth Shea, et al., "Immunologic Detection and Measurement of Glycated Apoliproprotein B With Site Specific Monoclonal Antibodies", *Journal of Immunological Methods*, vol. 162, No. 1, 4 Jun. 1993, Amsterdam, the Netherlands, pp. 85–95.

Van–Yu, Wu, et al., "Purification of Glycated Hemoglobin Free of Hemoglobin Alc and Its Use To Produce Monoclonal Antibodies Specific For Deoxyfructosyllsine Residues in Glycohemoglobin", *Biochemical and Biophysical Research Communications*, vol. 176, No. 1, 15 Apr. 1991, Duluth, MN, USA, pp. 207–212.

Y. Yamamoto, et al., "Radioimmunoassay of Glycated Serum Protein Using Monoclonal Antibody to Glucitollysine and Coomassie–Brilliant–Blue–Coated Polystyrene Beads", *Diabetes Research*, vol. 11, No. 1, May 1989, Edinburgh, GB, pp. 45–49.

L. Sorell, et al., "Monoclonal Antibodies Against Non–Enzimatically Glycated (NEG) Proteins. They use in Quantitative ELISA for NEG Serum Proteins Measurement", *Biotecnologia Aplicada*, vol. 9, No. 2, 1992, La Habana, Cuba, pp. 121–129.

Nakamura, et al., "Enzyme Immunoassays: Heterogeneous and Homogeneous Systems," vol. 1: *Immunochemistry*, pp. 27.1–27.20, ed. D. M. Weir, 4th ed., Blackwell Scientific Publications (1986).

Goldenberg, et al., "In vivo Imaging for the Detection of Human Tumors," *Cancer Imaging With Radiolabeled Antibodies*, pp. 273–292, Kluwer Academic Publishers (1990).

*Primary Examiner*—Toni R. Scheiner
*Assistant Examiner*—Nancy J. Parsons

[57] ABSTRACT

An antibody specifically immunoreactive with glycated LDL and methods for using the antibody are provided. The antibody can be used for quantitating amounts of glycated LDL in a sample, for monitoring glycemic control in diabetic patients, for diagnosing disease, for monitoring and diagnosing atherosclerotic cardiovascular disease, and for inhibiting accumulation of LDL cholesterol by cells in tissues subject to atherosclerotic disease.

18 Claims, No Drawings

MONOCLONAL ANTIBODIES AGAINST GLYCATED LOW DENSITY LIPOPROTEIN

This application is a continuation-in-part of application Ser. No. 07/903,955 filed Jun. 26, 1992, now abandoned.

TECHNICAL FIELD OF THE INVENTION

This invention is related to monoclonal antibodies against glycated LDL, hybrid cell lines producing these antibodies, and methods of using these monoclonal antibodies.

BACKGROUND OF THE INVENTION

Nonenzymatic glycation of low density lipoproteins (LDL), the major carrier of serum cholesterol, is a structural modification that affects the atherogenic potential of lipoproteins, and that increases the susceptibility of diabetic subjects to atherosclerotic complications. In particular, exposure to glycated LDL leads to intracellular accumulation of cholesterol esters, compromises the physiological ability of LDL to be metabolized by the LDL receptor pathway, and promotes uptake by alternative receptors leading to morphologic transformation of macrophages into foam cells.

Nonenzymatic glycation is a condensation reaction between carbohydrate and free amino groups at the amino-terminus or epsilon amino groups of lysine residues of proteins. The reaction is initiated with attachment of the aldehyde function of acyclic glucose to a protein amino group via nucleophilic addition, forming an aldimine, also known as a Schiff base. This intermediate product subsequently undergoes an Amadori rearrangement to form a 1-amino-1deoxyfructose derivative in stable ketoamine linkage, which in turn can cyclize to a ring structure (Cohen, M.P., *Diabetes and Protein Glycosylation,* Springer Verlag, 1986). This bimolecular condensation of free saccharide with protein constitutes a mechanism by which proteins are subject to post-ribosomal modification without the influence of enzymatic activities. In diabetic subjects, hyperglycemia promotes increased nonenzymatic glycation of both circulating and tissue proteins, thereby not only allowing the assessment of integrated glycemic control through determination of circulating glycated proteins, but also providing insight into the pathogenetic mechanisms responsible for the chronic complications associated with diabetes.

Glycation of LDL is pathogenetically contributory to the increased incidence of cardiovascular disease associated with diabetes. Incubation of human serum lipoproteins with glucose restilts in the covalent binding of glucose to ε-amino groups of lysine residues in the apolipoproteins of LDL, VLDL (very low density lipoproteins), and HDL (high density lipoproteins); glycation of the apolipoprotein B of LDL purified from the serum of diabetic patients is increased compared with levels of LDL glycation in samples from non-diabetic subjects. Binding and degradation of glycated LDL by cultured human fibroblasts and by umbilical vein endothelial cells is diminished compared with non-glycated LDL, and the degree of reduction in degradation is greater with increasing extent of glycation. The glycation of LDL abolishes the high affinity uptake and degradation process by normal skin fibroblasts, and also results in a decreased rate of clearance in vivo. In contrast to native LDL, which inhibits the activity of B-hydroxymethylglutaryl coenzyme A (HMG-CoA) reductase and stimulates acyl:CoA:cholesterol acyltransferase, glycated LDL does not affect these enzymes. Thus, disturbances in receptor-mediated internalization and degradation of LDL as a result of glycation also interfere with intracellular handling of cholesterol and regulation of its synthesis. This and other evidence indicates that glycation of lysine residues on apo-LDL, which is intimately involved with LDL receptor recognition, as a consequence of hyperglycemia alters LDL metabolism and contributes to atherogenesis in diabetic subjects. Further evidence comes from the finding that the internalization and degradation of LDL from patients with insulin-dependent diabetes and poor metabolic control is decreased compared with that of LDL isolated from normal subjects or from insulin-dependent diabetic patients with good metabolic control. Modification of only 2–5% of lysine residues in LDL, a modest level of glycation comparable to that observed in some diabetic individuals, is sufficient to produce demonstrable inhibition of LDL degradation by cultured fibroblasts and of the turnover of LDL injected into guinea pigs. Plasma apolipoproteins $A_1$, $A_2$, B, C and E all become glycated in hyperglycemic diabetic subjects.

Alteration of LDL by glycation is one of the biochemical mechanisms leading to the formation of macrophage-derived foam cells, the major histologic marker of atherosclerosis. Like certain other lipoprotein modifications such as acetylation and malondialdehyde alteration, glycation promotes clearance by subendothelial macrophages and results in intracellular deposition of lipoprotein-derived cholesterol. Modification of critical lysine residues of the apolipoprotein B protein of LDL produces internalization by the scavenger receptor of human monocyte-macrophages and the subsequent intracellular accumulation of lipoprotein-derived cholesterol ester.

The functional consequences of apo-LDL glycation and their role in the atherogenic process make it desirable to have reliable and specific methods to quantitate the amount of LDL glycation. Existing methods to measure glycated proteins include a colorimetric procedure based on reaction with thiobarbituric acid, affinity chromatography, high pressure liquid chromatography to measure furosine, and gel electrophoresis. Each of these tests has drawbacks relating to reproducibility, cost, expensive instrumentation, accuracy or other factors, and none is specific for glycated LDL as opposed to other glycated plasma proteins. Glycated albumin can be measured specifically with a monoclonal antibody that reacts with glycated epitopes residing in albumin but not in any other protein (U.S. Pat. No. 5,223,392). Tarsio (U.S. Pat. No. 4,797,473) describes monoclonal antibodies that react preferentially with glycated serum proteins. Glycated hemoglobin can be measured specifically with a monoclonal antibody that reacts with glycated epitopes residing in hemoglobin but not in any other protein (U.S. Pat. No. 5,183,739). Knowles et al (U.S. Pat. No. 4,727,036) produced antibodies for use in determining hemoglobin $A_{1c}$ but these antibodies do not react with glycated epitopes residing in other proteins or in hemoglobin at positions other than the N-terminus of the beta subunit. Other antibodies against glycated proteins described in the art only react if the glycated epitope has been converted to glucitol-lysine by borohydride reduction (Curtiss and Witzum, *J. Clin. Invest.* 72:1427, 1983; Nakayama et al., *J. Immunol. Meth.* 99:95, 1987, Curtiss and Witztum, *Diabetes* 34:452, 1985).

It would therefore be desirable to accurately and specifically quantify the amount of glycated LDL, since its measurement provides an index of risk for cardiovascular disease. It would also be desirable to have an agent that could identify glycated LDL deposited in tissues to diagnose atherosclerosis in vivo. It would further be desirable to have an agent that could prevent the internalization of glycated LDL by cells having the potential to become atherogenic foam cells.

SUMMARY OF THE INVENTION

It is an object of the present invention to provide a monoclonal antibody that is capable of reacting with the unique glycated epitope N-deoxyfructosyllysine present in glycated LDL.

It is another object of the present invention to provide methods for the diagnosis of disease using monoclonal antibodies which react with the unique glycated epitope present in glycated LDL but not in LDL or other proteins.

It is still another object of the present invention to provide a method for measurement of nonenzymatically glycated LDL.

Another object of the invention is to provide a method for monitoring glycemic control in patients with diabetes by measuring the amount of glycated LDL in their blood.

Yet another object of the invention is to provide a method for monitoring atherosclerotic cardiovascular disease by measuring the amount of glycated LDL in their blood.

Another object of the invention is to provide a method for directly measuring the amount of the unique glycated epitope N-deoxyfructose lysine in human LDL specimens.

Still another object of the invention to provide a method for diagnosing cardiovascular disease by detecting glycated LDL in tissues.

It is yet another object of the invention to provide a method for inhibiting the accumulation of LDL cholesterol by cells in tissues subject to atherosclerotic disease.

These and other objects of the invention are achieved by providing a monoclonal antibody that specifically binds to an epitope on glycated LDL comprising N-deoxyfructosyllysine which constitutes the glycated residues of LDL. The antibody does not bind to unglycated LDL or to other proteins, whether they are glycated or not. Thus, the epitope differs from those recognized by other antibodies described in the art in which the epitope is present in both unglycated and glycated forms of a protein (Tarsio et al., U.S. Pat. No. 4,797,473). The epitope identified by this monoclonal antibody is in the configuration in which it occurs in vivo such that there has been no artificial modification. Thus, the epitope differs from the sites recognized by other antibodies against glycated proteins described in the art, in which the epitope has been converted to glucitol-lysine by borohydride reduction (Curtiss and Witztum, *J. Clin. Invest.* 72:1427, 1983; Nakayama et al., *J. Immunol. Meth.* 99:95, 1987; Smith et al., U.S. Pat. No. 4,876,188).

DETAILED DESCRIPTION OF THE PREFERRED EMBODIMENTS

The present invention relates to monoclonal antibodies to glycated LDL. These monoclonal antibodies are highly useful for immunologic detection of glycated LDL associated with certain diseases as, for example, diabetes mellitus. The monoclonal antibodies are reactive with an epitope present on glycated LDL but are not reactive with unglycated LDL, nor with other proteins, whether glycated or not. The epitope identified by the antibody of the invention is not present on other proteins. In one particularly preferred embodiment of the invention the antibody is reactive with an epitope found on apolipoprotein B.

The present invention is based on the principle of specific immunologic recognition and reaction between a monoclonal antibody and the antigenic epitope to which the antibody uniquely and specifically binds. The recognition and binding can be detected, for example, by an ELISA type test, wherein the antibody is immobilized on a solid phase support, such as the bottom of a plastic well. A sample comprising human plasma or serum and enzyme-labeled reagent and enzyme substrate are contacted with the immobilized antibody so that antibody-antigen complexes form. Dilution, incubation and washing steps allow separation of bound and free reagents. A color forming reaction takes place as a result of binding of the antigen to antibody and the consequent reaction of the enzyme upon its substrate. The formation of color indicates the presence of glycated epitope in the test sample, and the intensity of the color provides a quantitative measure of the amount of glycated epitope in the sample. The ELISA type assay also may be performed by immobilizing antigen or sample and adding monoclonal antibody, enzyme labeled reagent and substrate, or adding enzyme-linked monoclonal antibody and test fluid and substrate. Of course, the antibody of the present invention can be used to measure glycated LDL in other immunological assay formats which are known in the art.

One particular monoclonal antibody of the present invention ES 12 was raised in mice which had been immunized with glycated LDL that had been prepared by incubation of the apolipoprotein B of LDL with glucose under nitrogen in the presence of EDTA. The antibody reacts with both synthetic (prepared in vitro) and native (in vivo) glycated LDL. This indicates that the antibody recognizes epsilon-D-fructose-lysine at sites along the protein of LDL that are common to in vitro and in vivo glycation. The antibody immunoreacts with glycated Apolipoprotein B (Apo B) purified from LDL, but does not immunoreact with unglycated Apo B or unglycated LDL. In addition, it is clear that there are steric or other conformational requirements in the epitopic recognition of glycated LDL since ES 12 does not recognize epsilon-D-fructose-lysine residues in other proteins.

Authentic glycated LDL or glycated Apo B (antigen) can be prepared by subjecting the LDL fraction of normal or diabetic human plasma or purified Apo B to affinity chromatography on phenylboronate to separate the unglycated LDL or Apo B from the glycated LDL or Apo B. Glycated proteins bind to phenylboronate because of affinity for the resin for cis-diol groups in sugars. The bound species are eluted with sorbitol, which acts to displace the bound sugar groups. See Day (1979)*J. Biol. Chem.* 254:9394; Travis (1976) *Biochem. J.* 157:301; and Wiley (1985) *Ann. Clin. Biochem.* 22:79. Authentic glycated LDL or glycated Apo B also can be prepared by incubating human LDL or Apo B for 5-7 days at 25° C. in a solution containing 500 mg/dL of glucose buffered in saline to pH 7.4. The preparation is dialyzed to remove free glucose, and subjected to the phenylboronate affinity chromatography purification procedure. Preferably, these manipulations are performed under nitrogen and/or in the presence of EDTA. The presence and purity of glycated LDL or Apo B can be confirmed with electrophoresis and with the thiobarbituric acid reaction for glucose in ketoamine linkage. See Ney (1981) *Anal. Biochem.* 118:294.

The purity of unglycated LDL or Apo B and the absence of glycated epitopes can be confirmed with electrophoresis and/or the thiobarbituric acid reaction. These procedures, together with the phenylboronate separation, ensure that the deoxyfructosyllysine is present on preparations of glycated LDL/Apo B and is absent from preparations of unglycated LDL/Apo B.

The general method used for production of hybridomas secreting monoclonal antibodies is well known to those of ordinary skill in the art. Illustrative of the techniques utilized in the practice of the present invention are those described in *Proceedings of the National Academy of Science USA*, 75:3405, 1979.

In brief, male BALB/c mice were immunized over a four-week period with glycated LDL prepared as described above (by incubation of the apolipoprotein B of LDL with glucose). After the final immunization, the animals were sacrificed and spleen cells fused with a mouse non-secretor myeloma cell line. Hybridomas were screened for antibody production and antibody-positive clones were tested for monoclonal antibody binding to glycated LDL. Of 76 fusion products, nine showed discrimination on initial screening between glycated and unglycated apolipoprotein B. Five were fully cloned and produce antibody which immunoreacts with glycated LDL but not unglycated LDL or other plasma proteins, whether glycated or not.

The isolation of other hybridomas secreting monoclonal antibodies with the specificity of the monoclonal antibodies of the invention can be accomplished by one of ordinary skill in the art by producing anti-idiotypic antibodies (Herlyn et al., *Science* 232:100, 1986) which can be used for screening. An anti-idiotypic antibody is an antibody which recognizes unique determinants present on the monoclonal antibody produced by the hybridoma of interest. These determinants are located in the hypervariable region of the antibody. It is this region which binds to a given epitope and, thus, is responsible for the specificity of the antibody. The anti-idiotypic antibody can be prepared by immunizing an animal with the monoclonal antibody of interest. The immunized animal will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunize the second animal, it is now possible to identify other clones producing antibodies with the same idiotype as the antibody of the hybridoma used for immunization and thereby greatly simplify and reduce the amount of screening needed to find other hybridomas secreting monoclonal antibodies with the specificity of the monoclonal antibodies of the invention.

Idiotypic identity between two monoclonal antibodies demonstrates that the two monoclonal antibodies are the same with respect to their recognition of the same epitopic determinant. Thus, by using anti-idiotypic antibodies to the epitopic determinants on a monoclonal antibody it is possible to identify other hybridomas expressing monoclonal antibodies of the same epitopic specificity.

Alternatively, it is possible to evaluate, without undue experimentation, a monoclonal antibody to determine whether it has the same specificity as the monoclonal antibody of the invention by determining whether the monoclonal antibody being tested prevents the monoclonal antibody of the invention from binding to a particular antigen with which the monoclonal antibody of the invention is normally reactive. If the monoclonal antibody being tested competes with the monoclonal antibody of the invention, as shown by a decrease in binding by the monoclonal antibody of the invention, then it is considered that the two monoclonal antibodies bind to the same epitope. Also, a monoclonal antibody can be tested for the same reactivity pattern for glycated LDL and for unglycated LDL and other proteins as the monoclonal antibody of the invention.

Under certain circumstances, monoclonal antibodies of one isotype might be more preferable than those of another in terms of their diagnostic or therapeutic efficacy. Particular isotypes of a monoclonal antibody can be prepared either directly, by selecting from the initial fusion, or prepared secondarily, from a parenteral hybridoma secreting monoclonal antibody of different isotype by using the sib selection technique to isolate class-switch variants (Steplewski et al., *Proc. Natl. Acad. Sci. USA* 80:8653, 1985; Spira et al., *J. Immunol. Meth.* 74:307, 1984). Thus, the monoclonal antibodies of the invention would include class-switch variants having the specificity of monoclonal antibody ES 12 which is produced by a hybridoma deposited at the American Type Culture Collection, 12301 Parklawn Drive, Rockville, Md. 20852.

The term "antibody" as used in this invention includes intact molecules as well as fragments thereof, such as, for example Fab and F(ab')$_2$. which are capable of binding the epitopic determinant. As used in this invention, the term "epitope" is meant to include any determinant capable of specific interaction with the monoclonal antibodies of the invention. Epitopic determinants usually consist of chemically active surface groupings of molecules such as amino acids or sugar side chains and usually have specific three-dimensional structural characteristics as well as specific characteristics.

The monoclonal antibodies of the invention are particularly suited for use in immunoassays in which they can be utilized in liquid phase or bound to a solid carrier. In addition, the monoclonal antibodies in these immunoassays can be detectably labeled in various ways. Examples of types of immunoassay which can utilize monoclonal antibodies of the invention are competitive and noncompetitive in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Regardless of the type of immunoassay which is used, the concentration of antibody utilized can be readily determined by one of skill in the art.

The monoclonal antibodies of the invention can be bound to many different carriers and used to detect the presence of the glycated LDL epitope identified by ES 12. Examples of well-known carders include glass, polystyrene, polyvinyl chloride, polypropylene, polyethylene, polycarbonate, dextran, amylases, natural and modified celluloses, polyacrylamides, agaroses and magnetite. The nature of the carrier can be either soluble or insoluble for purposes of the invention. Those skilled in the art will know of other suitable carriers for binding monoclonal antibody, or will be able to ascertain such, using routine experimentation. Particular solid substrates to which either antibodies or sample may be bound include microtiter plates and dipsticks.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

The monoclonal antibodies of the invention can be bound to many different labels known to those of ordinary skill in the art for in vivo detection of glycated LDL and thereby provide methods for diagnosis of atherosclerosis. Examples of imaging techniques to determine binding of the antibody to its epitope in situ are scintiscanning for radioisotopically labeled iodine, indium, or technetium. Most preferably, fragments such as Fab or F(ab') of the antibody would be used or the antibodies would be "humanized" as discussed below for this purpose.

The monoclonal antibodies of the present invention can be used to provide methods for inhibiting the internalization of glycated LDL by cells in tissues subject to atherosclerotic disease, and thereby provide treatment for atherosclerosis. Most preferably, for therapeutic use, the antibodies would be "humanized" by techniques described in the art. These techniques include chimerization wherein the antigen specific variable region of the mouse antibodies are joined to the constant (c) domains of human antibodies (Morrison et al., *Proc. Natl. Acad. Sci. USA* 81:6851, 1984; Morrison, Science 229:1202, 1985), and reshaping human antibodies by inserting the antigen-binding site (hypervariable loops) directly into a human antibody (Jones et al., *Nature* 321:522, 1986; Verhoyen et al., *Science* 239:1534, 1988; Reichmann et al., *Nature* 322:323, 1988).

For purposes of the invention, the glycated LDL epitope which is detected by the monoclonal antibodies of the present invention may be present in various biologic fluids and tissues. Any sample containing a detectable amount of glycated LDL can be used. Normally, a sample is a liquid such as plasma, blood, serum or the like, or a solid such as tissue, cells and the like. The glycated LDL epitope detected by the monoclonal antibodies of the invention may reside in situ in cells of the cardiovascular system such as endothelial cells, monocyte-macrophages, and the like.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinotrophenyl, pyroxidal, and fluorescein, which react with specific anti-hapten antibodies.

The antibodies of the present invention are diagnostically effective. That is to say that they can discriminate sufficiently between unglycated LDL and glycated LDL to provide and accurate measurement of the amount of glycated LDL in a human blood or tissue sample. Since the amount of unglycated LDL in human blood and cells is at least ten times the amount of glycated LDL, a diagnostically effective antibody that is suitable for quantitation of glycated LDL must be much more highly reactive with glycated LDL than with unglycated LDL. Most preferably the antibody recognizes an epitope present in glycated LDL but not present on unglycated LDL.

The antibodies of the present invention can distinguish between glycated LDL and other non-LDL proteins, whether or not these proteins are glycated. The epitope bound by the antibody is not present on other serum proteins. Especially significant is the ability of the monoclonal antibodies of the invention to specifically react with the glycated fructosyl-lysine epitope of glycated LDL but not to bind to any epitope common to unglycated LDL.

Monoclonal antibody ES 12 can be utilized in the present invention. ES12 is obtained from, or has the identifying characteristics of, an antibody from the cell line ES12 having ATCC accession number HB11251. The cell line is placed on deposit for 30 years at the American Type Tissue Culture Collection (ATCC), 12301 Parklawn Drive, Rockville, Md. 20852.

The above disclosure generally describes the present invention. A more complete understanding can be obtained by reference to the following specific examples which are provided herein for purposes of illustration only, and are not intended to limit the scope of the invention.

EXAMPLE 1:

Preparation of Hybridoma Cell Lines Producing Monoclonal Antibodies to Glycated LDL Male BALB/c mice were immunized with 100 µg of authentic glycated apolipoprotein B of LDL dissolved in 0.85% NaCl containing 1 mM EDTA (Ph 7.4), and mixed with Freund's complete adjuvant (1:1). The mixture was injected intraperitoneally. Seven days later, the mice were injected with antigen mixed with incomplete adjuvant (1:1), with antigert alone one week later, and then with antigen on three sequential days during the fourth week. On the day after the last injection, the animals were sacrificed and the spleens removed. The spleen cells were fused with SP 2/0 myeloma cells and the hybridoma colonies established according to standard techniques (Kennet, RH, McKearn, TJ and Bechtol, KB [eds]: *Monoclonal Antibodies: A New Dimension in Biological Analyses,* Plenum Press, New York and London, 1982). The resulting colonies with binding activity to glycated LDL were cloned at least four times by limiting dilution.

EXAMPLE 2:

Characterization of Monoclonal Antibodies Reactive with Glycated LDL

Triplicate individual samples of unglycated LDL and glycated LDL obtained as described above were subjected to agarose gel electrophoresis according to standard techniques. One of each triplicate set of gels was stained for protein and for lipid to determine the electrophoretic migration position of the different LDL preparations. The third gel of each set was transferred electrophoretically to nitrocellulose, blocked by soaking in a solution of 1% milk in 0.1M Tris buffered saline (Ph 8.0) for one hour and soaked for two hours in a solution of monoclonal antibody ES12 (10 ml of hybridoma culture supernatant) raised against glycated LDL. After washing, the nitrocellulose strips were then soaked in a 1:3000 solution of alkaline phosphatase-conjugated goat anti-mouse IgG antibody, followed after extensive washes with Tris/PBS by a solution of enzyme substrate and color developer. Electrophoretic transfer and immunoblotting were performed according to standard techniques. The nitrocellulose strips were examined for the presence and position of the monoclonal antibody to the antigen that it recognizes.

Unglycated and glycated LDL migrated to distinct positions on the gels, consistent with their differences in charge as a result of glycation of lysine amino groups. The migration position of unglycated LDL was identical when stained for protein or for lipid, and the migration position of glycated LDL was the same when stained for protein or for lipid.

Monoclonal antibody ES 12 did not bind to unglycated LDL as evidenced by the fact that no colored band could be visualized after electrophoretic transfer of this lipoprotein and its exposure to monoclonal antibody ES12, enzyme labeled reagent, and substrate. In contrast, monoclonal antibody ES12 specifically bound to authentic glycated LDL, as shown by the fact that a single colored band corresponding with the electrophoretic migration position of this antigen was visualized after its exposure to monoclonal antibody ES12 and enzyme labeled reagent and substrate.

As shown in these studies, monoclonal antibody ES12 specifically recognizes and binds to glycated LDL but not unglycated LDL. The recognition of and binding to glycated LDL by monoclonal antibody ES12 is specific for the N-1-deoxyfructosyl-lysine adduct since this epitope component is present on glycated LDL but not on unglycated LDL.

EXAMPLE 3:

Demonstration of Monoclonal Antibody Reactivity with Apo B

Triplicate individual samples of unglycated LDL or APO B and authentic glycated LDL or Apo B, obtained as described above, were subjected to SDS-polyacrylamide gel electrophoresis according to standard techniques. One of each set of gels was stained for protein to determine the electrophoretic position of the different preparations. The other two sets of gels were transferred electrophoretically to nitrocellulose and blocked as described in Example 2. One of these nitrocellulose transfers was then reacted with monoclonal antibody ES12, and the other was reacted with another monoclonal antibody know to specifically recognize the Apo B protein of LDL. After exposure to goat antimouse IgG, enzyme substrate, and color developer, the nitrocellulose strips were examined for the presence and position of colored protein bands, which indicate binding of the monoclonal antibodies to the antigens they recognize.

Monoclonal antibody ES 12 did not bind to unglycated LDL or Apo B not containing the deoxyfructosyl-lysine epitope as evidenced by the fact that no colored band could be visualized after electrophoretic transfer and exposure to monoclonal antibody ES 12, enzyme labeled reagent, and substrate. In contrast, monoclonal antibody ES12 specifically bound to authentic glycated LDL or Apo B, as shown by the fact that colored bands were visualized after their exposure to monoclonal antibody ES12 and enzyme labeled substrate and reagent. A colored band in the identical electrophoretic position was visualized after immunoreaction with another monoclonal antibody known to be specific for the Apo B protein of LDL, demonstrating co-identity of the glycated protein with the Apolipoprotein B of LDL.

As shown in these studies, monoclonal antibody ES12 specifically recognizes and binds to the glycated Apo B protein of LDL but not unglycated Apo B. The monoclonal antibody ES12 recognizes and binds to the N-deoxyfructosyllysine epitope on the Apo B protein of LDL, but does not recognize or bind to unglycated Apo B since it does not contain the N-deoxyfructosyl-lysine epitope.

EXAMPLE 4:

Detection of Glycated LDL in Human Plasma Using Monoclonal Antibody ES12

Samples of human plasma were electrophoresed on SDS-polyacrylamide gels, and electrophoretically transferred to nitrocellulose and immunoblotted according to the methods in Example 2.

Human plasma yielded, as expected, multiple protein bands with standard protein staining, ranging in molecular weight from about 20,000 to over 200,000. In contrast, only one band was visualized after electrophoretic transfer and reaction with monoclonal antibody ES 12 and enzyme labeled reagent and substrate. The location of this band, which represents the colored product formed upon reaction of the unique monoclonal antibody-antigen complex, coincided with that of authentic glycated apolipoprotein B. Thus, monoclonal antibody ES12 can specifically recognize and bind to glycated LDL in human plasma.

EXAMPLE 5:

Absence of Reactivity of ES12 with Glycated Proteins Other than Glycated LDL

Samples of human plasma, and of authentic glycated albumin or of authentic glycated hemoglobin (containing N-1-[1-deoxyfructosyl] lysine residues) were electrophoresed on SDS polyacrylamide gels and electrophoretically transferred to nitrocellulose and immunoblotted according to methods in Examples 2 and 3.

The protein band visualized in human plasma after immunoreaction with ES12 was shown, by immunoblotting with monoclonal antibody to Apo B as described in Example 3, to have co-identity with Apo B. Thus, monoclonal antibody ES12 recognizes and binds only to glycated apolipoprotein B in human plasma, even though plasma contains a multiplicity of proteins, some of which exist in glycated forms.

In contrast, no band was visualized after electrophoretic transfer of glycated albumin or glycated hemoglobin and reaction with monoclonal antibody ES12 and enzyme labeled reagent and substrate. Authentic glycated albumin yields a single band with standard protein staining of molecular weight 68,000, but no band was visualized on nitrocellulose immunoblotting with ES12. Authentic glycated hemoglobin yields toohomers, dimers and tetramers of molecular weight 16,000, 32,000 and 64,000 with standard protein staining, but no band was visualized on nitrocellulose immunoblotting with ES12. Thus, monoclonal antibody ES12 does not recognize or bind to glycated albumin or glycated hemoglobin even though these proteins contain deoxyfructosyl lysine adducts.

EXAMPLE 6:

Relative Reactivity of ES12 in Immunoassay with Glycated and Unglycated LDL/Apo B 500 ng of unglycated or glycated LDL/Apo B were immobilized onto plastic microtiter wells using carbonate-bicarbonate coupling buffer (Ph 9.6) for 18 hours at 25° C. After washing to remove unbound antigen, followed by blocking for four hours at room temperature with 1% milk in coupling buffer and washing, monoclonal antibody ES12 (100/μl of hybridoma culture supernatant) was added to each well and allowed to react for two hours. After washing with 0.1% Tween 20 in saline, alkaline phosphatase (AP)-conjugated goat anti-mouse IgG antibody in Tris/saline containing 0.1% milk was added and incubated for one hour at room temperature. After extensive washing, the presence and intensity of colored product were determined using AP substrate and amplifier system and read in an ELISA reader at an absorbance of 450 nm.

TABLE 1

| Antigen | Color Reaction (Absorbance) |
|---|---|
| Unglycated LDL or Apo B | 0.010 |
| Glycated LDL or Apo B | 0.760 |

As shown in Table 1, monoclonal antibody ES12 can selectively discriminate glycated from unglycated LDL or Apo B in an ELISA type immunoassay.

I claim:

1. A monoclonal antibody which specifically immunoreacts with an epitope comprising N-deoxyfructosyllysine, which epitope is present in glycated LDL (low density lipoprotein), but said epitope is not present in unglycated LDL or in other glycated or unglycated plasma proteins, wherein said epitope is present in apolipoprotein B of glycated LDL.

2. The antibody of claim 1 wherein the epitope present in glycated LDL retains its in vivo configuration, wherein said antibody was generated by the process of immunizing an animal with an immunogen comprising glycated apolipoprotein B of LDL.

3. The antibody of claim 1 which is ES12, produced by the hybridoma deposited at the ATCC as accession no. HB 11251.

4. A hybridoma which produces the antibody of claim 1.

5. The hybridoma of claim 4 which is ATCC accession no. HB11251.

6. A method for measuring the amount of glycated LDL in human serum or plasma, comprising the steps of:

contacting a sample comprising human serum or plasma with a monoclonal antibody according to claim 1, said contacting occurring under conditions which allow antibody-antigen complexes to form; and determining the amount of the antibody-antigen complexes, the amount of said complexes being proportional to the amount of glycated epitopes present in the glycated LDL of the sample.

7. The method of claim 6 wherein said antibody is immobilized on a solid support, and wherein (1) an enzyme-labeled reagent which specifically binds to glycated LDL and (2) an enzyme substrate are contacted with said antigen-antibody complexes to form a product, the amount of said product correlating with the amount of glycated LDL in the sample.

8. The method of claim 7 wherein the product is colored, and the intensity of the color provides a quantitative measure of the amount of glycated LDL in the sample.

9. The method of claim 6 wherein the sample is immobilized on a solid support, and said antibody is linked to an enzyme which reacts with a substrate to form a product, the amount of the product correlating with the amount of glycated LDL in the sample.

10. The method of claim 6 wherein the sample is immobilized on a solid support and the antigen-antibody complexes are contacted with (1) an enzyme-labeled reagent which specifically binds to said monoclonal antibody and (2) an enzyme substrate to form a product, the amount of the product correlating with the amount of glycated LDL in the sample.

11. The method of claim 7 wherein the enzyme-labeled reagent is an antibody specifically immunoreactive with an epitope present in glycated LDL (low density lipoprotein) but not in unglycated LDL or in other glycated or unglycated plasma proteins.

12. The method of claim 10 wherein the enzyme-labeled reagent is an antibody specifically immunoreactive with antibodies of the isotype of said monoclonal antibody.

13. A method for detecting glycated LDL in situ, comprising the steps of:

administering to a human a detectably labeled preparation comprising the antibody of claim 1 or fragments thereof which bind to epsilon-D-fructose-lysine on LDL;

scanning the human to obtain an image of the location of the detectably labeled antibody in the human.

14. The method of claim 13 wherein the preparation administered comprises Fab or F(ab') fragments.

15. The method of claim 13 wherein the preparation comprises a humanized mouse antibody.

16. The method of claim 6 wherein the antibody is ES12, produced by the hybridoma deposited at the ATCC as accession no. HB11251.

17. The method of claim 13 wherein the antibody is ES12, produced by the hybridoma deposited at the ATCC as accession no. HB11251.

18. The method of claim 6 wherein said monoclonal antibody was generated by the process of immunizing an animal with an immunogen comprising glycated LDL.

* * * * *